United States Patent
Ross

(10) Patent No.: US 6,428,508 B1
(45) Date of Patent: Aug. 6, 2002

(54) PULSED VACUUM CATARACT REMOVAL SYSTEM

(75) Inventor: Rod Ross, Mission Viejo, CA (US)

(73) Assignee: Enlighten Technologies, Inc., West Lake Village, CA (US)

( * ) Notice: Subject to any disclaimer, the term of this patent is extended or adjusted under 35 U.S.C. 154(b) by 0 days.

(21) Appl. No.: 09/495,633

(22) Filed: Feb. 1, 2000

(51) Int. Cl.$^7$ ................................................. A61M 1/00

(52) U.S. Cl. ........................ 604/118; 604/22; 604/35; 606/37

(58) Field of Search ........................... 604/22, 35, 118, 604/119, 120; 606/37–40, 170, 902

(56) References Cited

U.S. PATENT DOCUMENTS

| | | |
|---|---|---|
| 1,841,968 A | 1/1932 | Lowry |
| 1,847,658 A | 3/1932 | Lasker |
| 2,070,281 A | 2/1937 | Leggiadro |
| 2,480,737 A | 8/1949 | Jayle |
| RE23,496 E | 5/1952 | Seeler |
| 2,708,437 A | 5/1955 | Hutchins |
| 2,824,455 A | 2/1958 | Ristow et al. |
| 3,033,196 A | 5/1962 | Hay |
| 3,252,623 A | 5/1966 | Corbin et al. |
| 3,266,494 A | 8/1966 | Brownrigg et al. |
| 3,308,828 A | 3/1967 | Pippin |
| 3,399,677 A | 9/1968 | Gould et al. |
| 3,511,162 A | 5/1970 | Truhan |
| 3,561,429 A | 2/1971 | Jewett |
| 3,583,403 A | 6/1971 | Pohl |
| 3,589,363 A | 6/1971 | Banko |
| 3,624,821 A | 11/1971 | Henderson |
| 3,693,613 A | 9/1972 | Kelman |
| 3,723,030 A | 3/1973 | Gelfand |
| 3,752,161 A | 8/1973 | Bent |
| 3,763,862 A | 10/1973 | Spieth |
| 3,812,855 A | 5/1974 | Banko |
| 3,815,604 A | 6/1974 | O'Malley et al. |

(List continued on next page.)

FOREIGN PATENT DOCUMENTS

| | | |
|---|---|---|
| DE | 25 47 185 | 4/1977 |
| EP | 1033 120 A2 | 6/2000 |
| FR | 2 549 727 | 7/1963 |

OTHER PUBLICATIONS

Steinway Instrument Company Inc., The Steinway/Barraquer in–Situ Microkeratome Set.

Brochure, Site TXR Systems, Site Mycrosurgical Systems, Inc., Horsham, Pennsylvania.

Marshall M. Parks, "Intracapsular Aspiration" article, pp. 59–74.

Van Oldenborgh, "Correlation of late operative complication by means of a suction cutter", Opthal. Soc. U.K. (1980), 100, 219, PP. 219–221.

(List continued on next page.)

Primary Examiner—Charles R. Eloshway
Assistant Examiner—Tuan Nguyen
(74) Attorney, Agent, or Firm—Irell & Manella, LLP

(57) ABSTRACT

An ophthalmic cutter system that includes a cutter adapted to cut tissue such as a cataract lens and an irrigation handpiece adapted to hold the lens. The irrigation handpiece may be coupled to an irrigation system that introduces an irrigation fluid to the surgical site through the handpiece. The cutter may be coupled to an aspiration system that provides vacuum pulses to the surgical site. The vacuum pulses may pull tissue into a wire located at a distal end of a cutter cannula. The pulses may break and emulsify the tissue which is then aspirated through the cannula by the aspiration system. The wire may be connected to a controller that provides a current which is transformed into heat. The heat may assist in emulsifying the tissue.

7 Claims, 2 Drawing Sheets

U.S. PATENT DOCUMENTS

| | | |
|---|---|---|
| 3,841,799 A | 10/1974 | Spinosa et al. |
| 3,842,839 A | 10/1974 | Malis et al. |
| 3,882,872 A | 5/1975 | Douvas et al. |
| 3,884,238 A | 5/1975 | O'Malley et al. |
| 3,899,829 A | 8/1975 | Storm et al. |
| 3,903,881 A | 9/1975 | Weigl |
| 3,913,584 A | 10/1975 | Walchle et al. |
| 3,920,014 A | 11/1975 | Banko |
| 3,930,505 A | 1/1976 | Wallach |
| 3,977,425 A | 8/1976 | Hayashida |
| 3,982,539 A | 9/1976 | Muriot |
| 3,983,474 A | 9/1976 | Kuipers |
| 3,986,512 A | 10/1976 | Walliser |
| 4,004,590 A | 1/1977 | Muriot |
| 4,011,869 A | 3/1977 | Seiler, Jr. |
| 4,034,712 A | 7/1977 | Duncan |
| 4,043,342 A | 8/1977 | Morrison, Jr. |
| 4,108,182 A | 8/1978 | Hartman et al. |
| 4,135,515 A | 1/1979 | Muriot |
| 4,137,920 A | 2/1979 | Bonnet |
| 4,168,707 A | 9/1979 | Douvas et al. |
| 4,173,980 A | 11/1979 | Curtin |
| 4,178,707 A | 12/1979 | Littlefield |
| 4,204,328 A | 5/1980 | Kutner |
| 4,205,682 A | 6/1980 | Crock et al. |
| 4,210,146 A | 7/1980 | Banko |
| 4,217,993 A | 8/1980 | Jess et al. |
| 4,223,676 A | 9/1980 | Wuchinich et al. |
| 4,245,815 A | 1/1981 | Willis |
| 4,246,902 A | 1/1981 | Martinez |
| 4,274,411 A | 6/1981 | Dotson, Jr. |
| 4,301,802 A | 11/1981 | Poler |
| 4,304,262 A | 12/1981 | Icking |
| 4,308,385 A | 12/1981 | Goorden |
| 4,308,835 A | 1/1982 | Abbey |
| 4,314,560 A | 2/1982 | Helfgott et al. |
| 4,319,899 A | 3/1982 | Marsh |
| 4,320,761 A | 3/1982 | Haddad |
| 4,344,784 A | 8/1982 | Deckas et al. |
| 4,354,838 A | 10/1982 | Hoyer et al. |
| 4,395,258 A | 7/1983 | Wang et al. |
| 4,396,386 A | 8/1983 | Kurtz et al. |
| 4,427,427 A | 1/1984 | DeVecchi |
| 4,428,748 A | 1/1984 | Peyman et al. |
| 4,429,696 A | 2/1984 | Hanna |
| 4,445,517 A | 5/1984 | Feild |
| 4,474,411 A | 10/1984 | Peters et al. |
| 4,475,904 A | 10/1984 | Wang |
| 4,476,862 A | 10/1984 | Pao |
| 4,479,717 A | 10/1984 | Cornillault |
| 4,481,948 A | 11/1984 | Sole |
| 4,493,695 A | 1/1985 | Cook |
| 4,493,698 A | 1/1985 | Wang et al. |
| 4,522,371 A | 6/1985 | Fox et al. |
| 4,523,911 A | 6/1985 | Braetsch et al. |
| 4,524,948 A | 6/1985 | Hall |
| 4,530,357 A | 7/1985 | Pawloski et al. |
| 4,531,934 A | 7/1985 | Kossovsky et al. |
| 4,540,406 A | 9/1985 | Miles |
| 4,555,645 A | 11/1985 | Atkinson |
| 4,560,395 A | 12/1985 | Davis |
| 4,589,414 A | 5/1986 | Yoshida et al. |
| 4,598,729 A | 7/1986 | Naito et al. |
| 4,647,209 A | 3/1987 | Neukomm et al. |
| 4,660,556 A | 4/1987 | Swinger et al. |
| 4,660,970 A | 4/1987 | Ferrano |
| 4,662,370 A | 5/1987 | Hoffmann et al. |
| 4,665,914 A | 5/1987 | Tanne |
| 4,674,499 A | 6/1987 | Pao |
| 4,674,503 A | 6/1987 | Peyman et al. |
| 4,678,459 A | 7/1987 | Onik et al. |
| 4,688,570 A | 8/1987 | Kramer et al. |
| 4,690,099 A | 9/1987 | Gregan et al. |
| 4,701,049 A | 10/1987 | Beckmann et al. |
| 4,705,395 A | 11/1987 | Hageniers |
| 4,706,687 A | 11/1987 | Rogers |
| 4,723,545 A | 2/1988 | Nixon et al. |
| 4,743,770 A | 5/1988 | Lee |
| 4,757,814 A | 7/1988 | Wang et al. |
| 4,767,403 A | 8/1988 | Hodge |
| 4,768,506 A | 9/1988 | Parker et al. |
| 4,770,654 A | 9/1988 | Rogers et al. |
| 4,782,239 A | 11/1988 | Hirose et al. |
| 4,782,849 A | 11/1988 | Hodge |
| 4,791,934 A | 12/1988 | Brunnett |
| 4,805,615 A | 2/1989 | Carol |
| 4,805,616 A | 2/1989 | Pao |
| 4,807,623 A | 2/1989 | Lieberman |
| 4,819,635 A | 4/1989 | Shapiro |
| 4,825,191 A | 4/1989 | Breyer et al. |
| 4,828,306 A | 5/1989 | Blatt |
| 4,830,047 A | 5/1989 | Hodge |
| 4,837,857 A | 6/1989 | Scheller et al. |
| 4,838,281 A | 6/1989 | Rogers et al. |
| 4,840,175 A | 6/1989 | Peyman |
| 4,865,033 A | 9/1989 | Krumeich et al. |
| 4,884,570 A | 12/1989 | Krumeich et al. |
| 4,886,085 A | 12/1989 | Miller |
| 4,903,695 A | 2/1990 | Warner et al. |
| 4,909,815 A | 3/1990 | Meyer |
| RE33,250 E | 7/1990 | Cook |
| 4,943,289 A | 7/1990 | Goode et al. |
| 4,965,417 A | 10/1990 | Massie |
| 4,988,347 A | 1/1991 | Goode et al. |
| 4,997,437 A | 3/1991 | Grieshaber |
| 5,011,482 A | 4/1991 | Goode et al. |
| 5,013,310 A | 5/1991 | Goode et al. |
| 5,019,076 A | 5/1991 | Yamanashi et al. |
| 5,041,096 A * | 8/1991 | Beuchat et al. ............ 604/118 |
| 5,059,204 A | 10/1991 | Lawson et al. |
| 5,083,558 A | 1/1992 | Thomas et al. |
| 5,106,364 A | 4/1992 | Hayafuji et al. |
| 5,133,713 A | 7/1992 | Huang et al. |
| 5,133,726 A | 7/1992 | Ruiz et al. |
| 5,176,628 A | 1/1993 | Charles et al. |
| 5,201,749 A | 4/1993 | Sachse et al. |
| 5,207,683 A | 5/1993 | Goode et al. |
| 5,215,104 A | 6/1993 | Steinert |
| 5,217,459 A | 6/1993 | Kamerling |
| 5,226,910 A | 7/1993 | Kajiyama et al. |
| 5,242,404 A | 9/1993 | Conley et al. |
| 5,271,379 A | 12/1993 | Phan et al. |
| 5,273,406 A | 12/1993 | Feygin |
| 5,273,524 A | 12/1993 | Fox et al. |
| 5,285,795 A | 2/1994 | Ryan et al. |
| 5,322,505 A | 6/1994 | Krause et al. |
| 5,328,456 A * | 7/1994 | Horiguchi et al. ............ 604/22 |
| 5,330,470 A | 7/1994 | Hagen |
| 5,354,268 A | 10/1994 | Peterson et al. |
| 5,364,395 A | 11/1994 | West, Jr. |
| 5,374,188 A | 12/1994 | Frank et al. |
| 5,380,280 A | 1/1995 | Peterson |
| 5,383,454 A | 1/1995 | Bucholz |
| 5,395,368 A | 3/1995 | Ellman et al. |
| 5,403,276 A | 4/1995 | Schechter et al. |
| 5,403,311 A | 4/1995 | Abele et al. |
| 5,423,330 A * | 6/1995 | Lee ............................ 606/166 |
| 5,437,678 A | 8/1995 | Sorensen |
| 5,465,633 A | 11/1995 | Bernloehr |
| 5,474,532 A | 12/1995 | Steppe |
| 5,476,448 A | 12/1995 | Urich |

| | | |
|---|---|---|
| 5,476,473 A | 12/1995 | Heckele |
| 5,496,339 A | 3/1996 | Koepnick |
| 5,507,751 A | 4/1996 | Goode et al. |
| 5,520,684 A | 5/1996 | Imran |
| 5,527,332 A | 6/1996 | Clement |
| 5,527,356 A | 6/1996 | Peyman et al. |
| 5,531,744 A | 7/1996 | Nardella et al. |
| 5,556,397 A | 9/1996 | Long et al. |
| 5,566,681 A | 10/1996 | Manwaring et al. |
| 5,571,113 A * | 11/1996 | McDonald ................ 606/107 |
| RE35,421 E | 1/1997 | Ruiz et al. |
| D377,524 S | 1/1997 | Lipp |
| 5,611,799 A | 3/1997 | Smith |
| 5,624,394 A | 4/1997 | Barnitz et al. |
| 5,643,304 A | 7/1997 | Schechter et al. |
| 5,674,226 A * | 10/1997 | Doherty et al. ............ 604/44 |
| 5,693,013 A | 12/1997 | Geuder |
| 5,700,240 A | 12/1997 | Barwick, Jr. et al. |
| 5,704,927 A | 1/1998 | Gillette et al. |
| 5,738,677 A | 4/1998 | Colvard et al. |
| 5,779,723 A | 7/1998 | Schwind |
| 5,782,849 A | 7/1998 | Miller |
| 5,787,760 A | 8/1998 | Thorlakson |
| 5,795,328 A | 8/1998 | Barnitz et al. |
| 5,810,857 A | 9/1998 | Mackool |
| 5,814,010 A | 9/1998 | Ziegler |
| 5,817,034 A * | 10/1998 | Milliman et al. ......... 606/170 |
| 5,817,075 A | 10/1998 | Giungo |
| 5,868,728 A | 2/1999 | Giungo et al. |
| 5,916,330 A | 6/1999 | Jacobson |
| 5,941,250 A | 8/1999 | Aramant et al. |
| 5,944,731 A | 8/1999 | Hanna |
| 5,957,921 A | 9/1999 | Mirhashemi et al. |
| 5,989,272 A | 11/1999 | Barron et al. |
| 6,013,049 A | 1/2000 | Rockley et al. |
| 6,019,754 A | 2/2000 | Kawesch |
| 6,045,563 A | 4/2000 | Duprat |
| 6,051,009 A | 4/2000 | Hellenkamp et al. |
| 6,059,805 A | 5/2000 | Sugimura et al. |
| 6,083,236 A | 7/2000 | Feingold |
| 6,086,544 A | 7/2000 | Hibner et al. |
| 6,165,189 A | 12/2000 | Ziemer |
| 6,238,391 B1 * | 5/2001 | Olsen et al. ................ 604/35 |
| 6,245,084 B1 * | 6/2001 | Mark et al. ............... 606/170 |

OTHER PUBLICATIONS

Helfgott, M.D. "A System for Variable Aspiration of Material Dissected from the Posterior Chamber", Ophthalmic Surgery, vol. 15, Jun. 1984, pp. 529–350.

Coopervision Brochure on Cavitron/Kelman Model 6500 E.I.S. and Model 7500, 6 pages.

Surgical Design Brochure on "The Ocusystem", 1 page.

Coopervision Brochure on "Cavitron/Kelman Phaco–Emulsifier Aspirator Model 8001", 2 pages.

Coopervision Brochure on Cavitron/Kelman Phaco–Emulsifier Aspirator Model 9001, 6 pages.

Greishaber of Switzerland Brochure on "MPC, The Membrane Peeler Cutter", 5 pages.

Micro–Vit Vitrectomy System Product Brochure and Instruction Manual.

Storz Irrigation Aspiration System Product Brochure and Instruction Manual.

United Sugical Corporation Brochure on "Phacotron Plus", one page.

Surgical Design Company Brochure on Keates Ultrasonic I/E Mini Probe by A. Banko, 2 pages.

Surgical Design Corporation Brochure on U.S., Phaco System, 1 page.

Coopervision Brochure on System VI, 1 page.

Murayama et al. "A Portable Air Driving Unit for Blood Pumps", Japanese Journal of Artificial Organs, vol. 14, No. 3, pp. 1206–1209 (English Translation).

Scuderi, et al., French article entitled "La Chirurgie de la Cartaracte Congenitale", pp. 174–185. (English Translation).

Hayashi et al., Japanese Experience with Ventricular Assist Devices IBEE Engineering in Medicine and Biology Magazine Mar. 1986, pp. 30–36.

Grieshaber and Co. of Switzerland, "Sutherland Rotatable Intraocular Microscissors", 2 pages.

JCERS and Tissue Removal Systems, Diskecter™ System, Rapid Tissue Removal System advertisement.

Charles and Wang, "A Linear Suction Control for the Vitreous Cutter (Ocutome)", Arch. Ophthalmol. vol. 99, Sep. 1981, p. 1631.

Crosby, "On Control of Artificial Hearts", pp. 89–114.

Mrava, Cardiac Engineering, vol. 3, pp. 31–68.

* cited by examiner

PULSED VACUUM CATARACT REMOVAL SYSTEM

BACKGROUND OF THE INVENTION

1. Field of the Invention

The present invention relates to a system for removing tissue from the human body.

2. Background Information

Tissue, including cataract lenses, are typically removed with an ultrasonically driven handpiece. For example, in a cataract procedure, it is commonly referred to as phacoemulsification. A phaco handpiece includes a tip that is inserted through an incision formed in the cornea. The tip is oscillated by a driver unit at an ultrasonic frequency. The oscillating tip breaks and emulsifies the lens.

The tip is coupled to an irrigation system that introduces irrigation fluid into the anterior chamber of the eye. The irrigation fluid cools the tip and maintains the ocular pressure of the anterior chamber. The irrigation fluid flows through an annular channel formed between the oscillating tip and an external protective sleeve. The sleeve is typically constructed from a material with a low coefficient of thermal conductivity to reduce the amount of heat that flows into the cornea. Excessive heating may permanently damage the eye.

The tip is also coupled to an aspiration system that pulls the emulsified tissue and irrigation fluid out of the anterior chamber. The emulsified tissue and irrigation fluid flow through an inner channel in the oscillating tip.

An intraocular lens is implanted into the eye after the cataract lens is emulsified and removed. It is desirable to reduce the size of the incision formed in the eye to reduce post-operative complications. There have been developed intraocular lenses that can be inserted through an incision approximately 2.5 millimeters (mm). Most phaco tips require an incision of 3 mm. It is difficult to further reduce the diameter of both the tip and the outer sleeve of a phaco tip to fit the 2.5 mm profile. It would be desirable to provide an ophthalmic cutting system that would require an incision smaller than incisions formed in prior art procedures. It would also be desirable to provide an ophthalmic cutting system that did not generate heat at the corneal incision. Other types of procedures would be enhanced by similar improvements.

SUMMARY OF THE INVENTION

One embodiment of the present invention is an ophthalmic cutter system that includes a cutter adapted to cut tissue such as a cataract lens and an irrigation handpiece adapted to hold the lens. The irrigation handpiece may be coupled to an irrigation system that introduces an irrigation fluid to the surgical site through the handpiece. The cutter may be coupled to an aspiration system that provides vacuum pulses to the surgical site. The vacuum pulses may pull tissue into a wire located at a distal end of a cutter cannula. The pulses may break and emulsify the tissue which is then aspirated through the cannula by the aspiration system. The wire may be connected to a controller that provides a current which is transformed into heat. The heat may assist in emulsifying the tissue.

DETAILED DESCRIPTION

Figure 1:
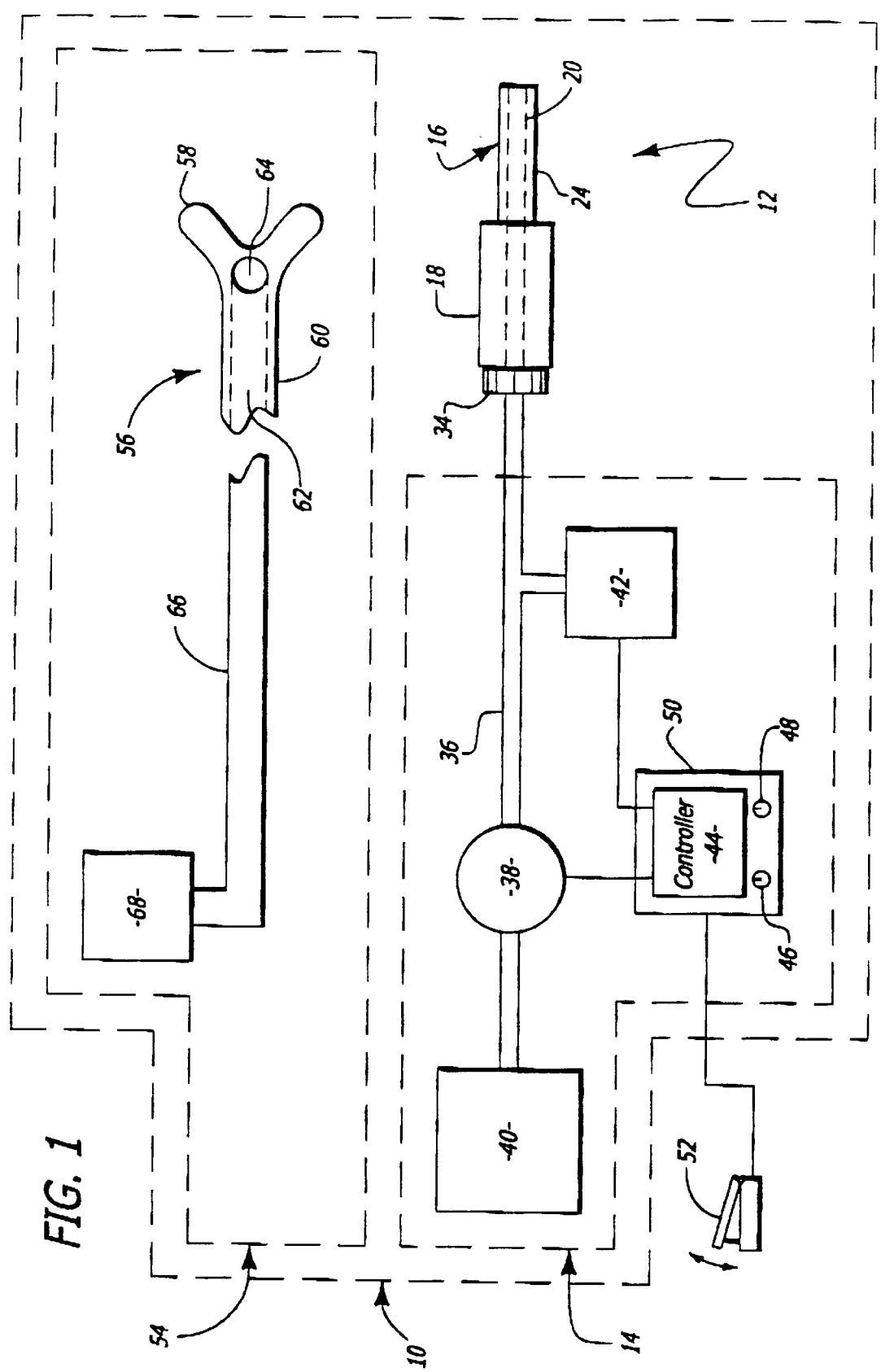
FIG. 1 is a schematic of an embodiment of an ophthalmic cutter system of the present invention.

Referring to the drawings more particularly by reference numbers, FIG. 1 shows an embodiment of an ophthalmic cutter system 10 of the present invention. The cutter system 10 may be used by a surgeon to cut and emulsify tissue. By way of example, the cutter system 10 may be employed to emulsify and aspirate a cataract lens within the eye.

The system 10 may include a cutter 12 that is coupled to an aspiration system 14. The cutter 12 may include a tip 16 that extends from a handpiece 18 adapted to be held by a surgeon. The tip 16 can be inserted into the eye to emulsify a lens.

Figure 2:
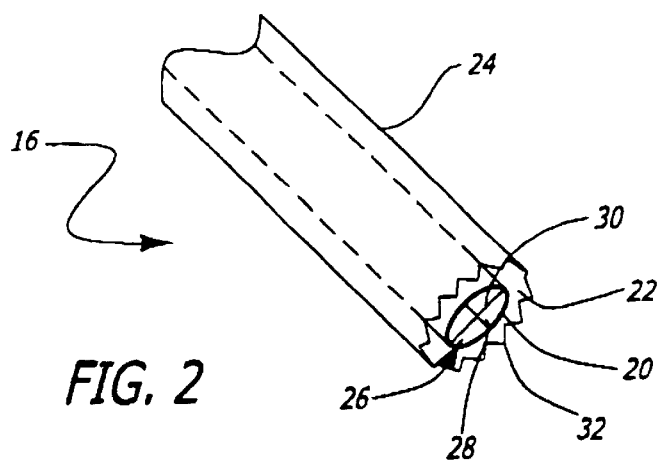
FIG. 2 is a perspective view of an embodiment of a cutter of the system.

FIG. 2 shows an embodiment of a cutter tip 16. The tip 16 may include an inner cannula 20 that extends through an inner passage 22 of an outer cannula 24. The inner cannula 20 may have an inner passage 26 in fluid communication with an opening 28 located at the distal end of the tip 16. The inner cannula 20 may have a wire or wires 30 that extend across the opening 28. Although a pair of wires is shown, it is to be understood that a different number of wires may be employed in the present invention.

The outer cannula 24 may have a plurality of teeth 32 that can become embedded into tissue. The outer cannula 24 may be fixed to the handpiece 18 shown in FIG. 1. The inner cannula 20 may be connected to a knob 34 that allows a surgeon to rotate the cannula 20. The cutter 12 may also have a bearing assembly (not shown) that allows the inner cannula 20 to rotate relative to the outer cannula 24. The inner cannula 20 may be rotated relative to the outer cannula 24 to induce a cutting action across the wires 30.

The aspiration system 14 may include an aspiration tube 36 that is coupled to the inner passage 26 of the inner cannula 20. The aspiration tube 36 is connected to a vacuum pump 38 and a collection canister 40. By way of example, the vacuum pump 38 may be a peristaltic pump. The vacuum pump 38 creates a vacuum pressure within the aspiration tube 36 and a flow of fluid from the opening 28 of the inner cannula 20 to the canister 40. The aspiration system 14 can pull emulsified tissue and fluid through the inner passage 26 and into the canister 40.

Figure 3:
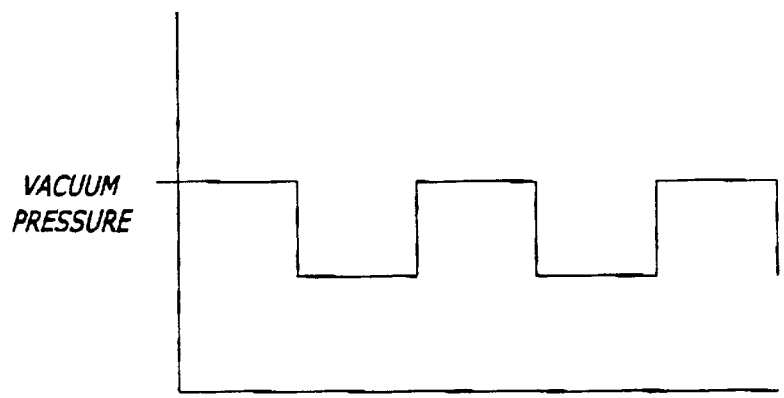
FIG. 3 is a graph showing vacuum pressure versus time within an aspiration line of the system.

The aspiration system 14 may also have a pulse generator or other device 42 that can create vacuum pulses within the aspiration tube 36 and the inner passage 26. The pulse generator 42 may create a series of vacuum pulses as shown in FIG. 3. The vacuum pulses reduce the pressure within the tube 36. Although square pulses are shown, it is to be understood that the pulses may have a variety of different waveforms. For example, the pulses may have a sawtooth waveform.

The pulse generator 42 and vacuum pump 38 may be connected to a controller 44. The controller 44 can control the speed of the pump 38 and the corresponding steady state vacuum pressure within the aspiration tube 36. The controller 44 can also control the repetition rate of the pulses generated by the pulse generator 42. The vacuum pressure and pulse rate can be varied by an operator through external knobs 46 and 48, respectively, located on a console 50. The vacuum pressure and pulse rate may also be controlled through a foot pedal 52 connected to the controller 44. The foot pedal 52 and controller 44 may operate in two modes. The steady state vacuum pressure may be varied in the first mode. The pulse rate may be varied in the second mode. The first mode can be initiated by depressing the foot pedal 52. Further depression of the foot pedal 52 may initiate the second mode. The system 10 may also be configured so that the operator can simultaneously vary the vacuum pressure and the pulse rate.

The controller 44 may also be electrically connected to the wire(s) 30. The controller 44 may provide a current to the wire(s) 30 to generate heat. The heat can assist in emulsifying the tissue. The current may be direct current (DC) or alternating current (AC) including AC current at a radio frequency (RF). The amplitude and/or frequency of the current can be controlled through the foot pedal 52 or knobs. Although a connection between the controller 44 and wire(s) 30 is described, it is to be understood that the heating element may be another element or device.

The system 10 may have an irrigation system 54. The irrigation system 54 may have an aspiration handpiece 56 adapted to hold the tissue during emulsification. The handpiece 56 may have a jaw portion 58 that extends from a handle portion 60. The handle portion 60 may be held by the surgeon. The handpiece 56 may further have an inner passage 62 that is in fluid communication with an opening 64. The inner passage 62 is in fluid communication with an irrigation tube 66. The irrigation tube 66 is connected to an irrigation bag 68. The irrigation bag 68 may gravity feed irrigation fluid into the inner passage 62 and through the opening 64.

In operation, the tip 16 may be inserted through an incision formed in the eye. Because the tip of the present invention does not have the outer sleeve typically found in phaco tip of the prior art, the tip 16 of the present invention may be constructed so that the incision is on the order of 1 millimeter. This incision size is smaller than incisions found in the prior art. Especially with respect to phaco procedures which utilize phaco devices that have an outer irrigation sleeve. The outer sleeve of phaco tips increases the overall diameter of the tips and the size of the incision. By eliminating the outer sleeve, the device of the present invention reduces the overall diameter of the tip and the size of the incision.

The irrigation handpiece 54 can be introduced into the anterior chamber through an opening separate from the incision used for the aspiration tip. The irrigation system 54 provides irrigation fluid to the anterior chamber to maintain the pressure therein. The vacuum pump 38 may be actuated to create a flow of fluid from the anterior chamber to the canister 40 by depressing the foot pedal 52. The surgeon can manipulate the tip 16 so that the teeth of the outer cannula 20 become embedded into the lens of the eye. The pulse generator 42 can be activated to create the vacuum pulses by further depressing the foot pedal 52. The vacuum pulses repetitively pull the lens into the wires to cut the lens tissue. The pulsing effect enhances the vacuum energy, resulting in added efficiency of tissue removal. The surgeon can also rotate the inner cannula to further induce cutting of the lens. The broken lens is then aspirated through the inner passage 26 and into the canister 40.

The present invention is to be distinguished from ultrasonically driven handpieces which move a tip into and out of the lens with energy referred to as cavitation. The movement of prior art tips relative to the outer protective sleeves generates heat that may damage the eye typically through thermal shrinkage of the cornea. The present invention pulls the lens into and away from the tip and thus does not generate the heat found in ultrasonically driven phaco tips of the prior art.

Figure 4:
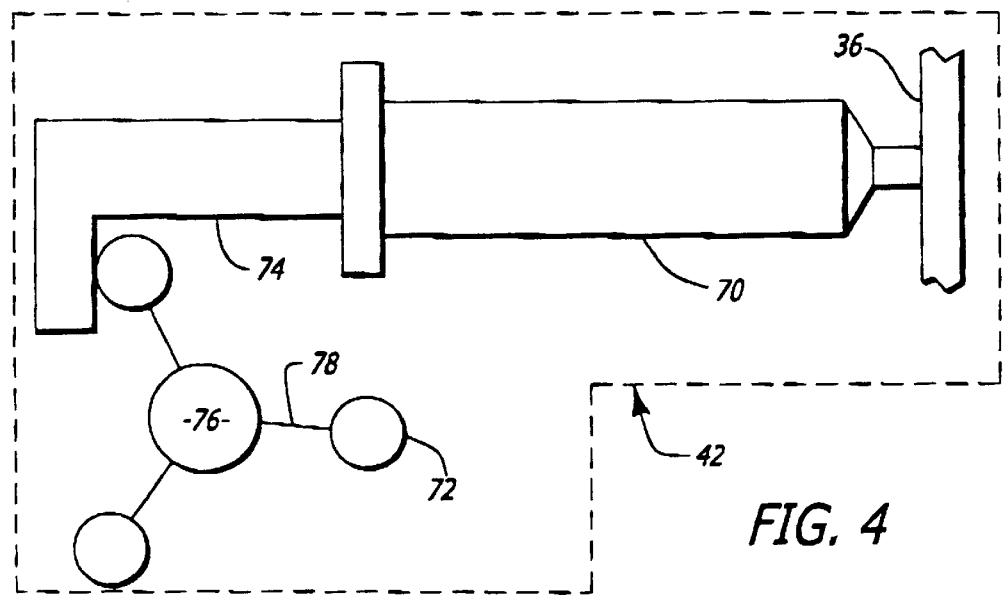
FIG. 4 is a top view of an embodiment of a pulse generator.

FIG. 4 shows an embodiment of a pulse generator 42. The generator 42 may include a syringe 70 that is connected to the aspiration tube 36. The generator 42 may further have a plurality of rotating weights 72 that repetitively strike a plunger 74 of the syringe 70. A vacuum pulse is created each time a weight engages the plunger 74. The weights 72 may be connected to a rotary motor 76 by a plurality of spring rods 78. The speed of the motor 76 can be controlled by the controller 44 shown in FIG. 1. The plunger 74 may be biased in an inward direction by a biasing spring (not shown).

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art.

For example, although the system 10 has been described for use in an eye, it is to be understood that the tip and other components can be used to cut, emulsify, etc. tissue in other areas. For example, the system could be used to perform procedures on a prostate or a spinal disk and liposuction.

What is claimed is:

1. A medical cutter, comprising:
   a first cannula that has an inner passage that is in fluid communication with a distal opening;
   a wire that extends across said distal opening;
   an aspiration tube that is in fluid communication with said inner passage;
   a vacuum generator adapted to create a vacuum pressure within said aspiration tube; and,
   a pulse generator adapted to create a plurality of vacuum pulses within said aspiration tube.

2. The cutter of claim 1, wherein the vacuum pulses decrease the pressure within said aspiration tube.

3. The cutter of claim wherein said pulse generator is coupled to an input device that can be manipulated to vary a repetition rate of the vacuum pulses.

4. The cutter of claim 3, wherein said input device is a foot pedal.

5. The cutter of claim 1, further comprising a second cannula that extends over said first cannula.

6. The cutter of claim 5, wherein said second cannula has a plurality of external teeth.

7. The cutter of claim 5, wherein said first cannula can be rotated within said second cannula.

* * * * *